US005789520A

United States Patent [19]
Karasawa et al.

[11] Patent Number: 5,789,520
[45] Date of Patent: Aug. 4, 1998

[54] CURING AGENT FOR RESINS AND RESIN COMPOSITION CONTAINING THE SAME

[75] Inventors: Minato Karasawa; Takeya Abe; Takuji Shimizu, all of Mobara; Takeshi Iwaki, Yokohama, all of Japan

[73] Assignee: Mitsui Chemicals, Inc., Tokyo, Japan

[21] Appl. No.: 769,519

[22] Filed: Dec. 19, 1996

[30] Foreign Application Priority Data

Dec. 27, 1995 [JP] Japan ................................ 7-340474
Dec. 27, 1995 [JP] Japan ................................ 7-340475

[51] Int. Cl.$^6$ ................... C07C 233/35; C07C 251/04; C08G 59/44
[52] U.S. Cl. ................... 528/122; 564/152; 564/153; 564/159; 564/160
[58] Field of Search .............. 528/122; 564/152, 564/153, 159, 160

[56] References Cited

U.S. PATENT DOCUMENTS

| 3,143,570 | 8/1964 | Caldwell et al. ............ 564/448 |
| 5,087,722 | 2/1992 | Inomata et al. ............ 558/338 |

FOREIGN PATENT DOCUMENTS

| 3202491 | 8/1983 | Germany . |
| 38-20975 | 10/1963 | Japan . |
| 54-004992 | 1/1979 | Japan . |
| 54-4992 | 1/1979 | Japan . |
| 61-12723 | 1/1986 | Japan . |
| 3-81255 | 4/1991 | Japan . |
| 3-95151 | 4/1991 | Japan . |
| 3-109361 | 5/1991 | Japan . |
| 3-181446 | 8/1991 | Japan . |
| 3-232850 | 10/1991 | Japan . |
| 4-224553 | 8/1992 | Japan . |
| 6-184082 | 7/1994 | Japan . |

OTHER PUBLICATIONS

Lee and Neville, "Handbook of Epoxy Resins", McGraw–Hill, third edition, Apr. 1967.

*Primary Examiner*—Frederick Krass
*Attorney, Agent, or Firm*—Burns, Doane, Swecker & Mathis, L.L.P.

[57] ABSTRACT

A curing agent having less odor and providing a cured resin which is excellent in appearance, mechanical properties, water resistance and chemical resistance, and a one-component type humidity-curing resin composition having excellent storage stability and providing a cured matter which is excellent in appearance and physical properties. Specifically, provided are polyaminoamide or ketimine obtained by dehydration of 2,5- and/or 2,6-bis(aminomethyl)-bicyclo[2.2.1]heptane with carboxylic acids or ketones, a curing agent for epoxy resins using the same and a one-component type humidity-curing epoxy resin or urethane prepolymer composition containing the curing agent.

6 Claims, No Drawings

CURING AGENT FOR RESINS AND RESIN COMPOSITION CONTAINING THE SAME

BACKGROUND OF THE INVENTION

(1). Field of the Invention

The present invention relates to a novel curing agent for resins, a production process for the same and uses thereof, more specifically to novel polyaminoamide or novel ketimine obtained by dehydration-condensation of 2,5-and/or 2,6-bis(aminomethyl)-bicyclo[2.2.1]heptane (hereinafter abbreviated as NBDA) with carboxylic acids or ketones, a production process for the same and an epoxy resin composition or a urethane resin composition containing them.

(2). Description of the Related Art

Aliphatic polyamines such as ethylenediamine and hexamethylenediamine have so far been used widely for a curing agent for epoxy resins for the reasons that they have high curing rates and can cause curing at room temperature and that they are liquid and therefore easy to handle. In general, however, aliphatic polyamines have the defects that they have high vapor pressures at room temperature and have an unpleasant odor and strong skin stimulation. Further, since they are liable to absorb carbon dioxide in the air to bring about whitening, so-called amine brushing of a cured matter, an appearance of a cured resin is damaged in many cases. In addition thereto, physical properties of the resulting cured resin, such as flexibility, fastness to bend, impact resistance and adhesive property, and water resistance and chemical resistances such as acid resistance are not necessarily high to a sufficient extent. Further, while they have the advantage that they have a high reactivity and can cause fast curing, a principal component and the curing agent each have to be weighed just before using, and therefore they have had a large problem on workability. Naturally, it has never been possible to use them for applications of a one-component type resin in which a premixture of a principal component and the curing agent is used for the sake of an enhancement in workability or for storage.

On the other hand, it is recognized that in general, alicyclic polyamines such as isophoronediamine and metaxylenediamine are advantageous from the viewpoint that they have lower vapor pressures and weak stimulation to skin as compared with aliphatic polyamines. However, the preceding defects of the aliphatic polyamines cannot completely be covered. It is shown in German Patent 3,202,491 that curing of a diglycidyl ether type resin of bisphenol with non-modified NBDA which is one of alicyclic polyamines proceeds rapidly at low temperature (50° C. or lower) and the cured resin has a high acid resistance. However, if NBDA is actually used for a curing agent in a non-modified form, it produces almost the same defects as those of the aliphatic polyamines described above, and it is not suited for one-component type uses as it is.

While aromatic polyamines such as metaphenylenediamine and 4,4'-diaminodiphenylmethane have a small basicity and weak stimulation to skin, they have low curing rates, and the majority of them are solid at room temperature. Accordingly, they have the defects that the workability is inferior and it is difficult to handle them. Usually, they do not cause curing at room temperature, and therefore they are applied mainly to hot-setting uses.

Accordingly, improvement by various modifications of aliphatic or alicyclic polyamines are usually tried in order to solve these defects. It is described in, for example, Japanese Patent Application Laid-Open No. Sho 54-4992 that a suitable reactivity is provided when using for a curing agent for an epoxy resin a compound obtained by reacting 0.5 to 2.0 moles of a monoepoxy compound or an acrylic compound with 1 mole of NBDA and the resulting epoxy resin can be improved in physical properties. That is, these modified matters have the merit to retard curing at room temperature to improve the workability, and a coated film which is hot-set therewith is evaluated to have a good impact resistance, fastness to bend and chemical resistance.

However, while curing is retarded at room temperature, the resulting cured resin is insufficient in terms of gloss, water resistance and is chemical resistance and inferior in flexibility and adhesive property. Further, while curing is retarded, it proceeds in due course, and therefore the above modifications can not be applied to a curing agent for one-component type resins in which principal components are blended in advance with the curing agent.

Some examples in which dicyandiamide, $BF_3$-amine complex, adipic acid hydrazide, imidazole derivatives and urea derivatives are used for one-component type latent curing agents for epoxy resins by blending in advance with epoxy resins are generally known, but they have the defect that heating at a high temperature for a long time is required for curing.

Curing agents making use of the fact that ketimines which are reaction products of amines with ketones isolate amines again by virtue of humidity (moisture) in the air are known as one-component type curing agents which are used by blending in advance with an epoxy resin. Examples of the preceding curing agents for epoxy resins are described in Japanese Patent Publication No. Sho 38-20975 and Japanese Patent Application Laid-Open No. Sho 61-12723, but there have been the defects that the quick drying property, the adhesive property and the thick film-coating property are inferior for a curing agent and a multistage process is required in order to obtain ketimine having intended performances.

With respect to urethane resins, adhesives, sealants, coating agents and paints each using a one-component type humidity-curing urethane resin are used for architectural uses because of convenience thereof. One-component type humidity-curing urethane resins which have so far been available make use of a reaction of polyisocyanate with humidity (moisture), that is, a reaction in which a part of the polyisocyanate groups is turned into amine by decarboxylation of a reaction product of isocyanate with water and resulting amine is reacted with the balance of the polyisocyanate groups to cause curing. However, according to the reaction mechanism when this active isocyanate is reacted with water, carbon dioxide is generated. Accordingly, there have been some cases where resulting carbon dioxide is cut off from an escape and causes foaming in the inside depending on use and a coating method thereof. This foaming brings about reduced strength and inferior appearance to produce a large problem.

SUMMARY OF THE INVENTION

An object of the present invention is to provide a curing agent for resins which has less odor and makes it possible to produce resins having excellent appearance, mechanical properties, water resistance and chemical resistance when used for curing.

Another object of the present invention is to provide a one-component type resin composition which causes quick curing by humidity at room temperature and provides a cured matter having excellent appearance and physical properties and which has excellent storage stability.

Intensive researches conducted by the present inventors in order to achieve the object described above has resulted in finding a quite novel polyaminoamide and ketimine obtained by dehydrate-condensation of NBDA with carboxylic acids or ketones.

This novel polyaminoamide has less odor, and an epoxy resin cured by using this has excellent appearance, mechanical properties, water resistance and chemical resistance.

In the case where novel ketimine is used as a one-component type curing agent for epoxy resins or urethane resins, the resulting one-component type resin composition is cured quickly by humidity at room temperature to provide a cured matter having excellent appearance and physical properties. Further, the one-component type resin composition has excellent storage stability.

The present invention relates to:

(1) a compound obtained by dehydration of 2,5- and/or 2,6-bis(aminomethyl)-bicyclo[2.2.1]heptane (norbornanediamine; hereinafter abbreviated as NBDA) with carboxylic acids or ketones, specifically, (2) the compound obtained by dehydration is polyaminoamide obtained by the reaction of NBDA with carboxylic acids, more specifically, (3) polyaminoamide obtained by the reaction of NBDA with polycarboxylic acids having 2 to 5 carboxyl groups in a molecule, (4) polyaminoamide obtained by the reaction of NBDA with tricarboxylic acids having 3 carboxyl groups in a molecule and having a saturated or unsaturated aliphatic hydrocarbon group having 1 to 60 carbon atoms or an alicyclic hydrocarbon group having 3 to 60 carbon atoms, particularly, (5) polyaminoamide represented by Formula (1), obtained by the reaction of NBDA with dicarboxylic acids having 2 carboxyl groups in a molecule:

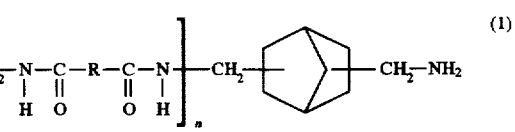

wherein R represents a saturated or unsaturated aliphatic hydrocarbon group having 1 to 60 carbon atoms or an alicyclic hydrocarbon group having 3 to 60 carbon atoms; n represents an integer of 0 to 2; and the position of two methylene groups bonded to a norbornane ring is either of a 2,5 position or a 2,6 position, and (6) polyaminoamide represented by Formula (2), obtained by the reaction of NBDA with monocarboxylic acids having one carboxyl group in a molecule:

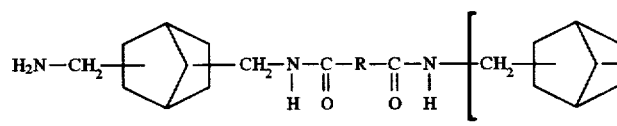

wherein R' represents a saturated or unsaturated aliphatic hydrocarbon group having 1 to 60 carbon atoms or an alicyclic hydrocarbon group having 3 to 60 carbon atoms; and the position of two methylene groups bonded to a norbornane ring is either of a 2,5 position or a 2,6 position, and these are (7) polyaminoamide obtained by reacting one equivalent of amino group in NBDA with 0.05 to 0.80 equivalent of the carboxyl group in the carboxylic acids.

Further, the compound obtained by dehydration is:

(8) ketimine obtained by the reaction of NBDA with ketones, more specifically, (9) ketimine represented by Formula (3), obtained by the reaction of NBDA with ketones:

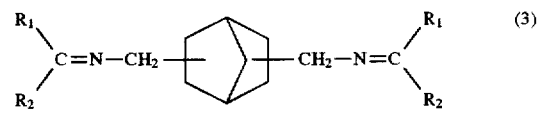

wherein $R_1$ and $R_2$ each represent a saturated or unsaturated aliphatic hydrocarbon group having 1 to 20 carbon atoms, an alicyclic hydrocarbon group having 3 to 20 carbon atoms or an aromatic hydrocarbon group having 6 to 20 carbon atoms; and the position of two methylene groups bonded to a norbornane ring is either of a 2,5 position or a 2,6 position, and

(10) ketimine obtained by reacting 1 mole of NBDA with 2.0 to 6.0 moles of the ketones.

Further, the present invention relates to:

(11) a curing agent for epoxy resins, characterized by containing any of the polyaminoamides described in the above (2) to (7),

(12) the epoxy resin composition containing the curing agent described in the above (11), characterized by being blended so that active hydrogen of an amino group contained in the curing agent is 0.5 to 1.5 equivalent per equivalent of an epoxy group contained in an epoxy resin to be cured,

(13) a curing agent for epoxy resins or urethane prepolymers, containing any of the ketimines described in the above (8) to (10),

(14) a one-component type humidity-curing epoxy resin composition containing the curing agent described in the above (13),

(15) the one-component type humidity-curing epoxy resin composition described in the above (14), characterized by containing 0.5 to 1.5 equivalent of an imino group in ketimine per equivalent of an epoxy group of the epoxy resin to be cured, further

(16) a one-component type humidity-curing urethane prepolymer composition containing the curing agent described in the above (13), and

(17) the one-component type humidity-curing urethane prepolymer composition described in the above (16), characterized by containing 0.5 to 1.5 equivalent of an imino group in ketimine per equivalent of an isocyanate group in the urethane prepolymer.

When novel polyaminoamide in the present invention is used as a curing agent for epoxy resins, the curing rate is fast, and the cured matter thereof has excellent appearance and is markedly excellent as well in mechanical properties, water resistance and chemical resistance.

When novel ketimine in the present invention is contained in a one-component type epoxy resin composition, the composition has the very excellent storage stability under storage cutting humidity off, but causes quick curing at room temperatures by contacting with humidity to provide the resulting cured matter with excellent appearance and physical properties. Further, a one-component type humidity-curing urethane resin composition containing ketimine of the present invention does not cause foaming in curing and provides a good coated film even when the film is thick.

DETAILED DESCRIPTION OF PREFERRED EMBODIMENTS

NBDA which is the principal raw material for the curing agent for epoxy resins of the present invention can be prepared by publicly known methods, for example, a method in which cyanonorbornene obtained by reacting dicyclopentadiene with acrylonitrile is reacted with hydrogen cyanide to obtain dicyanonorbornane, and then this is hydrogenated (described in Japanese Patent Application Laid-Open No. Hei 3-81255, Japanese Patent Application Laid-Open No. Hei 3-95151, Japanese Patent Application Laid-Open No. Hei 3-109361, Japanese Patent Application Laid-Open No. Hei 3-181446, Japanese Patent Application Laid-Open No. Hei 3-232850, Japanese Patent Application Laid-Open No. Hei 4-224553 and Japanese Patent Application Laid-Open No. Hei 6-184082). Any compound can be used for NBDA used in the present invention as long as the aminomethyl groups contained therein reside in a 2,5 position or a 2,6 position, and both may be mixed in any proportion.

Polycarboxylic acids used in the present invention include monocarboxylic acids or polycarboxylic acids such as dicarboxylic acids and polymerized fatty acids all of which have a saturated or unsaturated aliphatic hydrocarbon group having 1–60 carbon atoms, an alicyclic hydrocarbon group having 3–60 carbon atoms or an aromatic hydrocarbon group having 6–60 carbon atoms, and a mixture thereof. Monocarboxylic acids include, for example, saturated fatty acids such as acetic acid, butyric acid and stearic acid, and unsaturated fatty acids such as oleic acid, linoleic acid and linolenic acid. These monocarboxylic acids may be used in the form of a mixture of two or more kinds thereof, and preferred are fatty acids comprising mainly unsaturated fatty acids obtained from natural oil and fats and containing two or more acids described above, that is, tall oil fatty acid, soybean oil fatty acid and linseed oil fatty acid. Polycarboxylic acids include aliphatic dicarboxylic acids such as succinic acid, adipic acid, azelaic acid, sebacic acid and dodecanedioic acid, alicyclic dicarboxylic acids such as tetrahydro-phthalic acid and hexahydrophthalic acid, aromatic dicarboxylic acids such as phthalic acid, isophthalic acid and terephthalic acid, polymerized fatty acids, trimellitic acid, and an adduct of anhydrous castor oil fatty acid and acrylic acid. These polycarboxylic acids may be used in the form of a mixture of two or more kinds thereof or may be used in the form of a mixture with monocarboxylic acids. More preferred polycarboxylic acid is a polymerized fatty acid. This polymerized fatty acid is obtained by polymerizing unsaturated fatty acids such as oleic acid and linoleic acid and is a mixture containing known polybasic acids such as dimer acid (dicarboxylic acid) and trimer acid (tricarboxylic acid) and unreacted monocarboxylic acids. Examples of particularly preferred polymerized fatty acids include a mixture containing 1 to 15% by weight of monocarboxylic acid having 18 carbon atoms, 75 to 96% by weight of dimer acid having 36 carbon atoms and 3 to 21% by weight of trimer acid having 54 carbon atoms.

Polyaminoamide of the present invention is obtained usually by charging NBDA and carboxylic acids concurrently and reacting them, wherein the reaction temperature falls in a range of 120° to 250° C., preferably 150° to 250° C. The temperature lower than 120° C. retards the reaction and therefore is not practical. Meanwhile, the temperature exceeding 250° C. causes the reaction to go on quickly, but since the temperature exceeds the boiling point, it is difficult to carry out the reaction evenly over the whole reactants, and therefore such temperature is unsuitable. With respect to the reaction time, the reaction can be continued until it is completed, and the reaction time depends on the reaction conditions and therefore is not fixed. Usually, it falls in a range of 1 to 10 hours.

Polyaminoamide of the present invention can be obtained by distilling off excess NBDA and the reaction solvent when the solvent was used, by means of distillation under reduced pressure to isolate.

NBDA is reacted with carboxylic acids in such an equivalent ratio that the product has active amino hydrogens. They are reacted usually in a range of 0.05 to 0.80 equivalent, preferably 0.1 to 0.5 equivalent of the carboxyl groups of carboxylic acids based on one equivalent of the amino group contained in NBDA. If the reaction is carried out in the range of less than 0.5 equivalent, the resulting product is liable to have strong amine odor, and it is difficult to obtain the cured matter having excellent mechanical properties, water resistance and chemical resistance if it is used as a curing agent. If the reaction is carried out in the range exceeding 0.80 equivalent, gelation is liable to take place during the reaction, and therefore it is difficult to handle it. In addition thereto, it is difficult to obtain the good cured matter if it is used as a curing agent, and therefore the cured matter is liable to have deteriorated physical properties.

When polyaminoamide of the present invention is used as a curing agent for epoxy resins, it can be used as it is but is usually used in the form of a mixture with NBDA. In this case, NBDA may be added to isolated polyaminoamide. However, since usually excess NBDA is used in synthesis, it is efficient and preferred to omit a step for separating NBDA from polyaminoamide and use the reaction product as it is.

Further, the curing agent according to the present invention can be used in combination with other publicly known curing agents, for example, amine adduct curing agents, Michael adduct curing agents, aliphatic polyamines, polyamines having aromatic rings and alicyclic polyamines. In this case, if the amount used of the curing agent according to the present invention is usually 20% by weight or more based on the weight of the whole curing agent, the objects of the present invention can be achieved.

Polyaminoamide of the present invention may be used as a curing agent for epoxy resins as it is or can be used as well in combination with curing accelerators such as phenols and tertiary amines, and auxiliaries such as pigments, fillers, extenders, reinforcing agents and inert solvents. Examples of the suitable solvent include aromatic compounds such as toluene and xylene, alcohols such as methanol, ethanol, n-propanol, isopropanol, butanol and benzyl alcohol, and ketones such as acetone and methyl ethyl ketone. They can be used alone or in a mixture of a plurality thereof.

When the solvent is used for the curing agent for epoxy resins containing polyaminoamide of the present invention, the proportion of the solvent is 50% or less, preferably 30% or less based on the whole curing agent. If the proportion of the solvent exceeds 50%, the curing rate of the epoxy resins and the physical properties of the cured matters are notably reduced at room temperature or a low temperature because of the excessive proportion of the solvent, and therefore the performances are liable to be insufficient for curing agents.

When the curing agent containing polyaminoamide according to the present invention is used for the epoxy resins, the curing agent is blended in such an amount that active hydrogen of an amino group contained in the curing agent falls usually in a range of 0.5 to 1.5 equivalent, preferably 0.8 to 1.2 equivalent per equivalent of an epoxy group contained in the epoxy resin. If the active hydrogen of the amino group is less than 0.5 equivalent, the curing is carried out insufficiently, and the water resistance is liable to be reduced. Meanwhile, if the active hydrogen exceeds 1.5 equivalent, the epoxy resin is not completely cured. In addition, since the active hydrogen of the amino group remains in a large quantity, the water resistance is extremely lowered, and therefore such is not unsuitable.

When polyaminoamide of the present invention is used as the curing agent for epoxy resins, curing may be carried out either at room temperature or while heating.

The kinds of the epoxy resins for which polyaminoamide of the present invention can be used as the curing agent may be any one as long as they are epoxy resins having glycidyl groups capable of reacting with active hydrogens and include, for example, bisphenol A type epoxy resins, bisphenol F type epoxy resins, bisphenol AD type epoxy resins, urethane-modified epoxy resins having urethane bonds, novolak type epoxy resins, glycidyl ester type epoxy resins and glycidyl amine type epoxy resins. However, they shall not be restricted thereto. These resins may be a mixture of two or more kinds.

When polyaminoamide of the present invention is used as the curing agent for epoxy resins, the resulting resins have excellent curing rates, good appearance and very good flexibility, impact resistance, water resistance, chemical resistance and adhesive property. This can be applied to uses of, for example, paints, civil construction materials, adhesives, casting resins and laminates by using together with the epoxy resins.

Next, ketones which are raw materials for ketimine capable of being used as a curing agent in the present invention may be any one as long as they are compounds having a ketone group in a molecule and are preferably compounds having a saturated or unsaturated aliphatic hydrocarbon group having 1 to 20 carbon atoms, an aliphatic hydrocarbon group having 3 to 20 carbon atoms or an aromatic hydrocarbon group having 6–20 carbon atoms. They include, for example, ketones such as methyl ethyl ketone, methyl isobutyl ketone, dimethyl ketone, diethyl ketone, dipropyl ketone, dibutyl ketone, diisobutyl ketone, methyl isopropyl ketone, ethyl butyl ketone, methyl octyl ketone, dioctyl ketone, cyclohexanone, methyl cyclohexyl ketone, methoxymethyl butyl ketone, methyl cyclohexynyl ketone, aryl methyl ketone and acetophenone. However, they shall not be restricted thereto.

The reaction of NBDA with ketones is theoretically dehydration reaction of 2 moles of ketones with 1 mole of NBDA, and ketones of 2 moles or more are suitably used in the reaction. Usually, ketones are used and reacted preferably in a range of 2 to 6 moles per mole of NBDA. In this case, the reaction temperature falls usually in a range of 20° to 200° C. The reaction time depends on the reaction temperature and is not fixed. Usually, it falls in a range of 1 to 12 hours.

When ketimine of the present invention obtained by the reaction described above is used as a curing agent for epoxy resins, it is blended with the epoxy resins in such an amount that an imino group contained in ketimine of the present invention is 0.25 to 0.75 equivalent, preferably 0.4 to 0.6 equivalent per equivalent of an epoxy group contained in the epoxy resin. If this imino group is less than 0.25 equivalent, not only the curing rate is slow but also the curing in itself becomes insufficient. Meanwhile, if the imino group exceeds 0.75 equivalent, adverse influence is exerted on the physical properties (water resistance, mechanical strength and the like) of the cured matter, and therefore such is not preferred.

The kinds of the epoxy resins for which ketimine of the present invention can be used as the curing agent may be any one as long as they are epoxy resins having glycidyl groups capable of reacting with active hydrogens, and the examples thereof include bisphenol A type epoxy resins, bisphenol F type epoxy resins, bisphenol AD type epoxy resins, urethane-modified epoxy resins having urethane bonds, novolak type epoxy resins, glycidyl ester type epoxy resins and glycidyl amine type epoxy resins. However, they shall not be restricted thereto. A mixture of two or more kinds of these resins can be used.

Ketimine of the present invention can be applied to all uses of epoxy resins as the curing agent for epoxy resins. It is very useful for fields in which curing at room temperature and one-component type humidity-curing are particularly required, for example, paints, adhesives, sealing materials and the like.

When ketimine of the present invention is applied to, for example, the use of paints as the curing agent for epoxy resins, fillers such as talc, pigments such as red iron oxide, dispersants and plasticizers may be mixed. When ketimine of the present invention is applied to the use of adhesives as the curing agent for epoxy resins, additives such as plasticizers and fillers such as calcium carbonate may be mixed.

When ketimine of the present invention is applied to the use of sealing materials as the curing agent for epoxy resins, various additives for sealing materials may be used.

Ketimine of the present invention is mixed together with an epoxy resin and additives such as a filler, a plasticizer, a pigment and a dehydrating agent by conventional methods. The mixture is stored in a sealed vessel and can be used as a one-component type curing agent.

When ketimine of the present invention is used for a one-component type epoxy resin composition, a dehydrating agent such as a silane coupling agent and molecular sieve may coexist. When moisture infiltrates into the composition against the intention of users, the dehydrating agent is effective for preventing ketimine from forming amine.

Further, ketimine of the present invention can be used as a curing agent of a one-component type humidity-curing urethane prepolymer composition by mixing with a urethane prepolymer having plural active isocyanate groups.

Ketimine of the present invention contained in the composition described above is blended in such an amount that an imino group contained in ketimine is preferably 0.5 to 1.5 equivalent, more preferably 0.8 to 1.1 equivalent per equivalent of an active isocyanate group.

The urethane prepolymer used in the present invention is prepared by blending organic isocyanate containing two or more isocyanate groups in a molecule with a compound having at least one active hydrogen in a molecule so that a concentration (NCO %) of an active isocyanate group is 2 to 10% after finishing the reaction and then reacting them.

In the synthesis of the urethane prepolymer described above, the reaction temperature is preferably 50° to 120° C. In this reaction, a urethane catalyst may be used if necessary.

Organic isocyanate raw materials for this urethane prepolymer include 2,4-tolylenediisocyanate, 2,6-tolylenediisocyanate, phenylenediisocyanate, xylenediisocyanate, diphenylmethane-4,4'-diisocyanate, naphthylene-1,5-diisocyanate, hexamethylene-diisocyanate, isophoronediisocyanate, 1,3-bis(isocyanatomethyl)-cyclohexane, dicyclohexyl-methane-4,4'-diisocyanate, hydrogenated adducts of these isocyanates and isocyanurates of these isocyanates. These isocyanates and isocyanate derivatives may be used alone or in combination of two or more kinds thereof.

The compound having at least one active hydrogen in a molecule, which is another raw material includes alcohols such as methanol, ethanol, isopropyl alcohol, butanol, 2-butanol and t-butanol, hydroxyl group-containing fatty acids such as ricinoleic acid, glycols such as ethylene glycol, propylene glycol, butanediol, hexanediol, diethylene glycol, glycerin, hexanetriol, trimethylolpropane, pentaerythritol, polyethylene glycol, polypropylene glycol, polytetramethylene glycol, polyesterpolyol, polyoxypropylenediol, polyoxypropylenetriol, polycarbonatediol and acrylpolyol, and amines such as ethanolamine, propanolamine, dimethylethanolamine, dimethyl-propanolamine, ethylenediamine, hexamethylenediamine and γ-aminopropyltriethoxysilane. They may be used alone or in combination of two or more kinds thereof.

The urethane catalyst added according to necessity includes metal catalysts such as dibutyltin dilaurate and lead octylate, and tertiary amines such as triethylamine and N,N-(dimethylaminoethyl)morpholine.

The one-component type humidity-curing urethane resin composition using ketimine of the present invention can be applied to various uses as it is and is useful as, for example, a sealing material, a water resistance agent, a floor material, a wall material, an adhesive and a paint. Further, in order to control the viscosity, the resin properties and the durability, this composition can be used, if necessary, with fillers, thixo-providing agents, plasticizers, solvents, adhesives, colorants, stabilizers and cure-accelerating catalysts mixing. The resulting humidity-curing type urethane resin composition can be used immediately after prepared or can be stored by charging into a sealed can in nitrogen flow. The storage stability is good in a condition that the composition is isolated from moisture contained in the air in the sealed vessel. Even though the vessel is stored at a higher temperature than room temperature, the physical properties are kept at a high rate, and the viscosity stability is good as well. Once the vessel is opened, the composition is exposed to moisture contained in the air to be cured quickly and can provide a non-foamed urethane resin having excellent mechanical properties unlike conventional humidity-curing urethane resins.

EXAMPLES

Polyaminoamides and ketimines of the present invention shall be explained below in further detail with reference to referential examples, examples and comparative examples. However, the present invention shall not be restricted thereto. In the following examples, "part", "%" and "ppm" are based on weight.

Referential Example 1 (Preparation of NBDA)
1) Synthesis of Cyanonorbornene

Dicyclopentadiene of 54.2%, acrylonitrile of 45.8% and hydroquinone of 500 ppm as a polymerization inhibitor were mixed, and this mixed solution was continuously fed into a tubular reactor (inner diameter: 8 mm) at a rate of 50 ml/hr, wherein the reaction temperature was controlled to 153° C. in a residence time of the reaction solution of up to 5 hours, 170° C. in a residence time of up to 7 hours and 180° C. in a residence time of up to 9 hours. After this reaction reached a steady state, the reaction was further continued for 20 hours to obtain crude cyanonorbornene of about 1 liter having a purity of 95%. This was concentrated under reduced pressure to distill off unreacted cyclopentadiene and acrylonitrile, whereby cyanonorbornene of 950 g having a purity of 99.6% was obtained.

2) Synthesis of Dicyanonorbornane

A round bottom flask (glass-made; content volume 300 ml; equipped with a stirrer, a thermometer, a nitrogen-introducing tube, a heater and a cooler) was charged with tetrakis(triphenylphosphite)nickel of 2.48 g, zinc chloride of 0.27 g and triphenylphosphite of 2.48 g as catalysts and cyanonorbornene of 240 g obtained as described above, and the space part of the flask was substituted with nitrogen at room temperature. Then, the flask was maintained at 85° C. while stirring to dissolve the catalysts.

Next, nitrogen gas was introduced into a vessel charged with liquid hydrogen cyanide which is cooled on ice water and bubbled to generate hydrogen cyanide gas. Hydrogen cyanide of total 59 g was fed into the solution contained in the flask over the period of 5 hours to react. The reaction liquids obtained by three operations in all with repeating more twice the same operation as that described above were blended to obtain crude dicyanonorbornane having a purity of 97%.

Further, this crude dicyanonorbornane was aerated with nitrogen gas at a rate of 500 ml/minute for 1 hour, and then insoluble matters were filtered off. A round bottom flask (glass-made; content volume 2 liters; equipped with a stirrer, a thermometer, a nitrogen-introducing tube, a heater and a cooler) was charged with the filtrate of 800 g thus obtained and toluene of 240 g, and then a 8% sodium hydroxide aqueous solution of 160 g was added, thereto followed by heating at 50° C. for 1 hour while stirring. A half or 600 g of the resulting solution was transferred into a separating funnel (content volume: 2 liters), and toluene of 680 g was added to extract dicyanonorbornane. Then, an organic phase containing it was shaken with water of 400 g for washing, and this washing was repeated three times. The balance 600 g of the solution was treated in the separating funnel in the same manner as that described above to obtain a toluene solution of about 2400 g in all containing dicyanonorbornane of 33%.

3) Synthesis of NBDA

An autoclave (stainless steel-made, content volume: 3 liters, magnetic stirring type) was charged with 2000 g of the toluene solution containing 33% dicyanonorbornane obtained above and a Raney cobalt catalyst of 13.2 g, and then liquid ammonia of 137 g was fed thereto. Further, hydrogen was pressed thereinto by applying pressure so as to be an initial hydrogen pressure of 70 kg/cm$^2$·G to carry out catalytic hydrogenation at 150° C. while stirring. After finishing the reaction, the catalyst was filtered off, and then NBDA was separated from toluene by distillation under reduced pressure to obtain NBDA of about 600 g having a purity of 99.8%.

Example 1 (Synthesis of Polyaminoamide (1))

A reactor equipped with a stirrer, a thermometer and a condenser was charged with NBDA of 154 g and adipic acid of 29.2 g, and the temperature was elevated to 160° C. under nitrogen atmosphere to carry out the reaction for 2 hours while distilling off condensation water. Then, the temperature was raised to 200° C., and the reaction was further continued for 2 hours. The termination of the reaction was judged by confirming that the distilled amount of condensation water reached the theoretical amount and that carboxylic acid (absorption by a carbonyl group of a carboxylic acid: 1700 cm$^{-1}$) disappeared and polyaminoamide (absorption by a carbonyl group of an amide bond: 1643 cm$^{-1}$) was produced by means of infrared absorption spectrum analysis. Excess NBDA was distilled off from this reaction solution under reduced pressure to obtain polyaminoamide involved in the present invention (hereinafter abbreviated as polyaminoamide (1)) (yield: 97%).

The results of elemental analysis, infrared absorption analysis and mass spectrometry of polyaminoamide (1) are shown below:

| Elemental analysis: | C | H | N |
|---|---|---|---|
| Measured value: | 68.13 | 10.27 | 13.28 |
| Theoretical value*[1]: | 68.86 | 10.11 | 13.38 |

*[1]: case of R = (CH$_2$)$_4$ and n = 0 in Formula (1)

Infrared absorption spectrum: Absorption based on a carbonyl group of an amide bond: 1643 cm$^{-1}$; Mass spectrometry: [M+H]$^+$=419

Example 2 (Synthesis of Polyaminoamide (2))

The reactor was charged with NBDA of 154 g and Versadyme 216 (brand name; Henkel Hakusui Co., Ltd.) of 119 g which is a dimer acid, and the temperature was elevated to 170° C. under nitrogen atmosphere to carry out the reaction for 2 hours while distilling off condensation water. Then, the temperature was raised to 200° C., and the reaction was further continued for 2 hours. The termination of the reaction was confirmed in the same manner as that in Example 1, and excess NBDA was distilled off under reduced pressure to obtain polyaminoamide involved in the present invention (hereinafter abbreviated as polyaminoamide (2)) (yield: 95%).

The results of elemental analysis, infrared absorption analysis and mass spectrometry of polyaminoamide (2) are shown below:

| Elemental analysis: | C | H | N |
|---|---|---|---|
| Measured value: | 77.35 | 11.25 | 6.50 |
| Theoretical value*[1]: | 77.77 | 11.79 | 6.57 |

*[1]: calculated on the basis of the composition of

Barsadum 216:

monomer acid 8% dimer acid 77% trimer acid 15%

Infrared absorption spectrum: Absorption based on a carbonyl group of an amide bond: 1644 cm$^{-1}$; Mass spectrometry: [M+H]$^+$=836

Example 3 (synthesis of polyaminoamide (3))

The reactor was charged with NBDA of 154 g and Aliphat 47 (brand name; Henkel Hakusui Co., Ltd.) of 64 g which is a monocarboxylic acid, and the temperature was elevated to 160° C. under nitrogen atmosphere to carry out the reaction for 2 hours while distilling off condensation water. Then, the temperature was raised to 200° C., and the reaction was further continued for 2 hours. The termination of the reaction was confirmed in the same manner as that in Example 1, and excess NBDA was distilled off under reduced pressure to obtain polyaminoamide involved in the present invention (hereinafter abbreviated as polyaminoamide (3)) (yield: 95%).

The results of elemental analysis, infrared absorption analysis and mass spectrometry of polyaminoamide (3) are shown below:

| Elemental analysis: | C | H | N |
|---|---|---|---|
| Measured value: | 77.33 | 11.65 | 6.25 |
| Theoretical value*[1]: | 77.12 | 12.19 | 6.71 |

*[1]: calculated on the basis of the composition of

Aliphat 47:

| C$_{16}$ saturated monocaboxylic acid | 10% |
|---|---|
| C$_{18}$ saturated monocaboxylic acid | 55% |
| C$_{18}$ unsaturated monocaboxylic acid (number of double bond: 1) | 31% |
| C$_{18}$ unsaturated monocaboxylic acid (number of double bond: 2) | 4% |

Infrared absorption spectrum:

Absorption based on a carbonyl group of an amide bond: 1644 cm$^{-1}$; Mass spectrometry: [M+H]$^+$=419, 421

Example 4

The reaction solution of NBDA and adipic acid obtained in Example 1 of 25 parts by weight per 100 parts by weight of Epikote 828 (brand name; Yuka Shell Epoxy Co., Ltd., epoxy equivalent: 190 g/eq) which is a bisphenol A type epoxy resin was used as it was without distilling NBDA off to cure the resin.

Example 5

The reaction solution of NBDA and Versadyme 216 obtained in Example 2 of 39 parts by weight per 100 parts by weight of Epikote 828 which is a bisphenol A type epoxy resin was used as it was without distilling NBDA off to cure the resin.

Example 6

The reaction solution of NBDA and Aliphat 47 obtained in Example 3 of 27 parts by weight per 100 parts by weight of Epikote 828 which is a bisphenol A type epoxy resin was used as it was without distilling NBDA off to cure the resin.

Example 7

Other new curing agent of 55 parts by weight prepared by mixing the reaction solution (a mixture of excess NBDA and polyaminoamide (2)) obtained in Example 3 with benzyl alcohol so that a ratio of the reaction solution/benzyl alcohol was 7/3 was used for Epikote 828 of 100 parts by weight which is a bisphenol A type epoxy resin to cure the resin.

Comparative Example 1

The same procedure as that in Example 1 was repeated, except that the charged amount of adipic acid was changed to 146 g, but the reaction solution was gelled, and it was impossible to use this as a curing agent.

Comparative Example 2

The same procedure as that in Example 1 was repeated to obtain a curing agent, except that the charged amount of adipic acid was changed to 2.9 g. This curing agent of 21 parts by weight per 100 parts by weight of Epikote 828 which is a bisphenol A type epoxy resin was used to cure the resin.

Comparative Example 3

NBDA itself of 20 parts by weight per 100 parts by weight of Epikote 828 which is a bisphenol A type epoxy resin was used to cure the resin.

Comparative Example 4

Isophoronediamine, which is an alicyclic diamine, (Vestamin IPD, brand name; Huels Co., Ltd.) of 23 parts by weight per 100 parts by weight of Epikote 828 which is a bisphenol A type epoxy resin was used to cure the resin.

The cured matters were prepared in the following manner; each of the curing agents obtained in Examples 1 to 3 and the curing agents obtained in Comparative Examples 2 to 4 was mixed with an epoxy resin and defoamed for 3 minutes under a pressure of 20 Torr; then, the mixture was applied on a cold-rolled steel plate or a glass plate (only for a water resistance test) to a thickness of 200 μm by means of a doctor blade and left for standing at room temperature (25° C.) and 80% RH for 7 days to cure the film, whereby a test piece was prepared. This coated film was evaluated for the following items.

1) Curing Rate:

An epoxy resin (Epikote 828) and the curing agent were blended in the prescribed amounts under a constant temperature of 25° C. Then, a vessel was charged with the mixture of 50 g and tightly sealed after installing a thermocouple thermometer to determine time (minutes) spent for achieving a maximum temperature of the exothermic reaction.

2) Drying Time:

According to JIS K-5400, determined was time (hours) spent from immediately after forming the coated film till a dent was not marked or the coated film was not felt to move by nipping strongly the test piece (steel plate) in the center thereof between a thumb and a forefinger and scratches were not marked on the coated film by rubbing repeatedly the center of the coated film quickly with a fingertip.

3) Evaluation of the Physical Properties of the Cured Matters

Pencil Hardness:

This is based on a pencil scratching test of JIS K-5400.6.14. That is, a lead of a pencil was applied on the coated film of the test piece (steel plate) at an angle of 45°, and the film is scratched with the pencil at a load of 1 kg, wherein the above procedure is repeated five times per one hardness in order from a pencil having a soft hardness, and a hardness at which the film is broken twice or more is recorded.

Appearance:

The surface of the coated film of the test piece is observed with the naked eye to evaluate it by four grades:

◎ well glossy, ○ glossy, Δ reduced in gloss, x whitening

Water Resistance and Chemical Resistance:

A test piece is dipped in water, an aqueous solution or an organic solvent shown in Table 1 and Table 2 at room temperature for 7 days, and the appearance of the coated film is observed with the naked eye to evaluate it by four grades:

◎ well glossy, ○ slightly reduced in gloss,

Δ a little inferior, x markedly inferior

Adherence Property

Evaluation was carried out according to a cross-cut adhesion test of JIS K-5400.6.15. That is, 11 parallel lines each in length and breadth are drawn on the coated film of the test piece at a space of 1 mm by means of a cutter and a cutter guide to mark checkered cuts thereon so that 100 squares are formed in an area of 1 cm². A cellophane adhesive tape is pressed strongly thereon, and the number of squares remaining after peeling the tape off is recorded.

Flexibility:

A steel-made hemi-sphere is pressed against the back face of a test piece having a coated film by means of an Erichsen tester to determine a pushed-out distance (mm) of the hemi-sphere at which cracking and peeling are observed on the coated film.

Impact Resistance:

The impact resistance was tested according to JIS K-5400.6.13.3B. A test piece is put between an impact piece which has a radius of 6.35±0.03 mm and is round at the tip thereof and a pedestal having a dent corresponding to the round part, wherein a weight of 500 g is dropped from the upper part, and the height (cm) at which the coated film of the test piece is broken is determined.

3) Adhesion Test:

An epoxy resin is blended with the curing agent in the prescribed amounts, and then the blended matter is defoamed and applied on two sheets of cold-rolled steel plates (100 mm×25 mm×1.6 mm) in an adhesion area of 25 mm×12.5 mm, followed by curing at 25° C. for 7 days to prepare a sample for the adhesion test. The sample is measured for a tensile shear adhesive strength (kgf/cm²).

The test results, physical properties of the cured matters and appearance of the coated films are shown in Table 1 and Table 2.

TABLE 1

Performances of curing agents prepared in Examples 4 to 7

| | Example | | | |
|---|---|---|---|---|
| | 4 | 5 | 6 | 7 |
| Epikote 828 (parts) | 100 | 100 | 100 | 100 |
| Curing agent (parts) | 25 | 39 | 27 | 55 |
| Curing rate (minutes) | 35 | 28 | 30 | 34 |
| Drying time (hours) | 5.0 | 4.5 | 5.0 | 3.5 |
| Appearance | ◎ | ◎ | ◎ | ◎ |
| Pencil hardness | 2H | 2H | 2H | 2H |
| Adherence ( /100) | 90 | 100 | 100 | 100 |
| Flexibility (mm) | 4.0 | 6.2 | 4.8 | 8.5 |
| Impact test (cm) | 30 | 35 | 30 | >50 |
| Water resistance | ◎ | ◎ | ◎ | ◎ |
| Chemical resistance | | | | |
| 10% sodium hydroxide aqueous solution | ○ | ◎ | ◎ | ◎ |
| 10% sulfuric acid aqueous solution | ○ | ◎ | ◎ | ◎ |
| 5% sodium chloride aqueous solution | ○ | ◎ | ◎ | ◎ |
| Methanol | ○ | ◎ | ◎ | ◎ |
| Hexane | ◎ | ◎ | ◎ | ◎ |
| Toluene | ◎ | ◎ | ◎ | ◎ |
| Tensile shear adhesive strength (kgf/cm²) | 70 | 87 | 94 | 138 |

TABLE 2

Performances of curing agents prepared in Comparative Examples 2 to 4

|  | Comparative Example | | |
|---|---|---|---|
|  | 2 | 3 | 4 |
| Epikote 828 (parts) | 100 | 100 | 100 |
| Curing agent (parts) | 21 | 20 | 23 |
| Curing rate (minutes) | 40 | 35 | 77 |
| Drying time (hours) | * | * | 7.0 |
| Appearance | Δ | Δ | ○ |
| Pencil hardness | * | * | HB |
| Adherence ( /100) | 80 | 80 | 0 |
| Flexibility (mm) | 0.4 | 0.2 | 0.1 |
| Impact test (cm) | 5 | 5 | 5> |
| Water resistance | x | x | Δ |
| Chemical resistance |  |  |  |
| 10% sodium hydroxide aqueous solution | Δ | Δ | ○ |
| 10% sulfuric acid aqueous solution | x | x | Δ |
| 5% sodium chloride aqueous solution | x | x | x |
| Methanol | Δ | Δ | Δ |
| Hexane | Δ | Δ | Δ |
| Toluene | Δ | Δ | Δ |
| Tensile shear adhesive strength (kgf/cm$^2$) | 35 | 31 | 15 |

*Impossible to measure

Example 8 (Synthesis of Ketimine (1))

A four neck flask of 1 liter equipped with a stirrer, a thermometer and a reflux tube having a separator was charged with NBDA of 154 g and methyl isobutyl ketone of 400 g, and the space part of the flask was substituted with nitrogen. Then, they were reacted at 100° to 120° C. for 8 hours, and water generated by condensation during the reaction was drawn out of the separator and removed. The completion of the reaction was judged by confirming that the distilled amount of condensation water reached the theoretical amount and that an amino group (absorption by an amino group of NBDA: 3364, 3285 and 1603 cm$^{-1}$) disappeared and an imino group (1660 cm$^{-1}$) was formed by means of infrared absorption spectrum analysis. After confirming that NBDA was completely reacted, excess ketone was distilled off under reduced pressure to obtain ketimine involved in the present invention (hereinafter, this ketimine shall be abbreviated as ketimine (1)) (yield: 96%).

The results of elemental analysis, infrared absorption analysis and mass spectrometry of ketimine (1) are shown below:

| Elemental analysis: | C | H | N |
|---|---|---|---|
| Measured value: | 78.53 | 12.10 | 9.35 |
| Theoretical value*$^1$: | 79.15 | 12.03 | 8.80 |

*$^1$: case of R$_1$ = CH$_3$ and R$_2$ = CH$_2$CH(CH$_3$)CH$_3$ in Formula (3)

Infrared absorption spectrum: Absorption based on an imino group: 1660 cm$^{-1}$; Mass spectrometry: |M+H|$^+$=319

Example 9 (Synthesis of Ketimine (2))

A four neck flask of 1 liter equipped with a stirrer, a thermometer and a reflux tube having a separator was charged with NBDA of 154 g and diethyl ketone of 344 g as ketone, and the space part of the flask was substituted with nitrogen. Then, they were reacted at 100° to 115° C. for 8 hours, and water generated by condensation during the reaction was drawn out of the separator and removed. The termination of the reaction was judged in the same manner as that in Example 8. After confirming that NBDA was completely reacted, excess ketone was distilled off under reduced pressure to obtain ketimine involved in the present invention (hereinafter, this ketimine shall be abbreviated as ketimine (2)) (yield: 95%).

The results of elemental analysis, infrared absorption analysis and mass spectrometry of ketimine (2) are shown below:

| Elemental analysis: | C | H | N |
|---|---|---|---|
| Measured value: | 78.03 | 11.63 | 9.52 |
| Theoretical value*$^1$: | 78.55 | 11.80 | 9.65 |

*$^1$: calculated on the basis of R$_1$ = R$_2$ = CH$_2$CH$_3$ in Formula (3)

Infrared absorption spectrum: Absorption based on an imino group: 1662 cm$^{-1}$; Mass spectrometry: |M+H|$^+$=291

Example 10

The ketimine compound (1) obtained in Example 8 of 42 parts by weight per 100 parts by weight of Epikote 828 which is a bisphenol A type epoxy resin was used to cure the resin.

Example 11

The ketimine compound (2) obtained in Example 9 of 38 parts by weight per 100 parts by weight of Epikote 828 which is a bisphenol A type epoxy resin was used to cure the resin.

Comparative Example 5

NBDA itself of 20 parts by weight per 100 parts by weight of Epikote 828 was used without using the ketimine compound (1) obtained in Example 8 to cure the resin.

Comparative Example 6

Meta-xylylene diamine, MXDA (brand name; Mitsubishi Gas Chemicals, Co. Ltd.) of 136 g instead of NBDA in Example 8 and methyl isobutyl ketone of 400 g were reacted under the same conditions as those in Example 8 to obtain ketimine (3) (yield 93%).

This ketimine (3) of 39 parts by weight per 100 parts by weight of Epikote 828 was used to cure the resin.

The curing rates and the physical properties of the cured matters prepared in Examples 10 to 11 and Comparative Examples 5 to 6 were evaluated in the following manners.

Each of ketimine compounds (1) to (3) and NBDA used as the curing agents was kneaded with the epoxy resin in a blend ratio defined in Examples 10 to 11 and Comparative Examples 5 to 6, and the kneaded matter was defoamed under a pressure of 20 Torr for 3 minutes. Then, the kneaded matter was applied on a cold-rolled steel plate or a glass plate (only for a water resistance test) to a thickness of 500 μm by means of a doctor blade and left for standing at room temperature (25° C.) and 80% RH for 7 days to cure the film, whereby a test piece was prepared. This coated film was evaluated for the following items.

1) Curing Rate:

A pencil hardness of the coated film was measured every fixed time.

2) Physical Properties of the Cured Matter:

Appearance, water resistance, adherence, flexibility and impact resistance were evaluated according to the methods employed in Examples 4 to 7 and Comparative Examples 2 to 4.

3) Evaluation of Storage Stability:

The compositions having the blend ratios shown in Table 3 were put into a sample bottle (with a tight stopper) substituted with nitrogen and left for standing in an atmosphere of 40° C. for 5 days. Then, the states of the compositions were observed.

The results thereof are shown in Table 3.

TABLE 3

Performances of curing agents prepared in
Examples 10 to 11 and Comparative Examples 5 to 6

|  |  | Example |  | Comparative Example |  |
|---|---|---|---|---|---|
|  |  | 10 | 11 | 5 | 6 |
| Epikote 828 (parts) |  | 100 | 100 | 100 | 100 |
| Curing agent (parts) |  | 42 | 38 | 20 | 39 |
| Pencil hardness | after 1 day | B | HB | * | 6B |
|  | after 4 days | H | H | * | 5B |
|  | after 7 days | 2H | 2H | * | 4B |
| Appearance |  | ⊚ | ⊚ | Δ | x |
| Adherence ( /100) |  | 100 | 100 | 80 | 80 |
| Flexibility (min) |  | 1.4 | 1.0 | 0.2 | 0.6 |
| Impact test (cm) |  | 25 | 20 | 5 | 20 |
| Water resistance |  | ⊚ | ⊚ | x | x |
| Storage stability |  | NC | NC | GL | NC |

*Impossible to measure
NC: No change
GL: Gelation after starting the test

Referential Example 2 (Synthesis of Urethane Prepolymer)

A reactor which is usable in reduced pressure and has a stirrer was charged with polyoxypropylenediol having a molecular weight of 3000, Diol-3000 (brand name; Mitsui Toatsu Chemicals, Inc.) of 518 parts, polyoxypropylenetriol having a molecular weight of 5000, MN-5000 (brand name; Mitsui Toatsu Chemicals, Inc.) of 222 parts, MDI-PH (brand name; Mitsui Toatsu Chemicals, Inc.) of 246 parts and dibutyltin dilaurate, Neostan U-100 (brand name, Nitto Kasei Co., Ltd.) of 0.02 part. Stirring was carried out while passing dry nitrogen or under reduced pressure so that moisture in the atmosphere was not mixed in. An oil bath was used while taking care of heat generation to elevate the temperature to 80° C. Stirring was continued for 2 hours while keeping the conditions, and then the temperature was reduced down to 40° C. or lower to take out the content, whereby a urethane prepolymer containing active isocyanate of 6.0% was obtained.

Example 12

The urethane prepolymer in Referential Example 2 was used to carry out a test in order to show the effect of ketimine of the present invention. A frame of 50 mm×50 mm was formed on a releasing paper with wood chips having a thickness of about 10 mm, and a mixture obtained by blending the urethane prepolymer of 50 parts prepared in Referential Example 2 with ketimine compound (1) of 6 parts was poured into this frame to form a film having a thickness of 2 mm. This was left for standing at a constant temperature of 20° C. or 40° C. and at a constant relative humidity of 65% in either case for 7 days, and then the state of foaming was observed. Further, a No. 2 dumbbell-form test piece was prepared to carry out a tensile test according to JIS K-6301.

Example 13

Evaluation was carried out in the same manner as that in Example 12, except that the thickness of the film was changed to 8 mm.

Comparative Example 7

Evaluation was carried out in the same manner as that in Example 12, except that instead of ketimine compound (1), dibutyltin dilaurate of 0.025 parts was used.

Comparative Example 8

Evaluation was carried out in the same manner as that in Example 13, except that instead of ketimine compound (1), dibutyltin dilaurate of 0.025 parts was used.

The results obtained in Examples 12 and 13 and Comparative Examples 7 and 8 are summarized in Table 4.

TABLE 4

Examples 12 to 13 and Comparative Examples 7 to 8

|  | Example |  | Comparative Example |  |
|---|---|---|---|---|
|  | 12 | 13 | 7 | 8 |
| Urethane prepolymer prepared in Referential Example 2 (parts) | 50 | 50 | 50 | 50 |
| Ketimine compound (1) (parts) | 6 | 6 | 0 | 0 |
| Dibutyltin dilaurate (parts) | 0 | 0 | 0.025 | 0.025 |
| Film thickness (mm) | 2 | 8 | 2 | 8 |
| State at 20° C. | NF | NF | F | F |
| State at 40° C. | NF | SF | F | MF |
| Tensile strength (MPa) | 25.5 | — | 7.5 | — |
| Elongation percentage (%) | 180 | — | 83 | — |

NF: no foaming
F: foaming
SF: scarcely foaming
MF: markedly foaming

What is claimed is:

1. A polyaminoamide obtained by dehydration of 2,5- and/or 2,6-bis(aminomethyl)-bicyclo[2.2.1]heptane (hereinafter abbreviated as NBDA) with carboxylic acids, the polyaminoamide being obtained by reacting one equivalent of amino group in the NBDA with 0.05 to 0.80 equivalent of carboxyl group in the carboxylic acids.

2. Polyaminoamide as described in claim 1, obtained by the reaction of NBDA with polycarboxylic acids having 2 to 5 carboxyl groups.

3. Polyaminoamide as described in claim 2, obtained by the reaction of NBDA with tricarboxylic acids having a saturated or unsaturated aliphatic hydrocarbon group having 1 to 60 carbon atoms or an alicyclic hydrocarbon group having 3 to 60 carbon atoms.

4. Polyaminoamide as described in claim 2 which is represented by Formula (1) and is obtained by the reaction of NBDA with dicarboxylic acids:

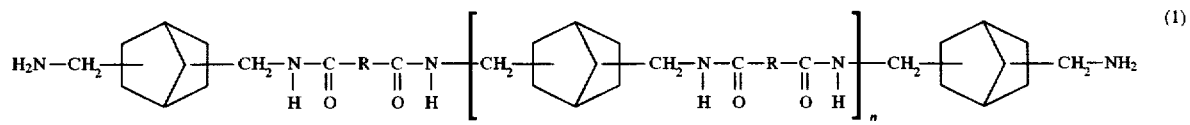
(1)

wherein R represents a saturated or unsaturated aliphatic hydrocarbon group having 1 to 60 carbon atoms or an alicyclic hydrocarbon group having 3 to 60 carbon atoms; n represents an integer of 0 to 2; and the position of two methylene groups bonded to the norbornane ring is either 2,5 or 2,6.

5. A curing agent for epoxy resins, containing the polyaminoamide described in claim 1.

6. An epoxy resin composition containing the curing agent described in claim 5, which has been blended so that the active amino hydrogen contained in the curing agent comprises 0.5 to 1.5 equivalent per equivalent of epoxy group contained in the epoxy resin to be cured.

* * * * *

UNITED STATES PATENT AND TRADEMARK OFFICE
CERTIFICATE OF CORRECTION

PATENT NO. : 5,789,520
DATED : August 4, 1998
INVENTOR(S) : Minato KARASAWA et al It is certified that error appears in the above-identified patent and that said Letters Patent is hereby corrected as shown below:

1) As set forth in the Petition Under 37 C.F.R. §1.48(b)(1) which was filed on May 26, 1998 and granted on September 1, 1998, please <u>delete</u> the following inventor from the inventive entity:

Takeshi IWAKI, Yokohama, Japan

2) As set forth in the Supplemental Information Disclosure Statement filed on July 15, 1997 and initialled by the Examiner in February of 1998, please insert the following prior art references:

<u>U.S. Patent Documents</u>
| | | |
|---|---|---|
| 4,501,864 | 2/85 | Higginbottom |

<u>Foreign Patent Documents</u>
| | | |
|---|---|---|
| 2324673 | 4/77 | France |
| 0469751 | 2/92 | Europe |
| 1064841 | 1/64 | Great Britain |
| 0654465 | 5/95 | Europe |

Signed and Sealed this

Eighth Day of June, 1999

Attest:

Q. TODD DICKINSON

Attesting Officer      Acting Commissioner of Patents and Trademarks